United States Patent
Rao et al.

(10) Patent No.: US 7,015,359 B1
(45) Date of Patent: Mar. 21, 2006

(54) VAPOR PHASE CATALYTIC PROCESS FOR SIMULTANEOUS FURFURAL HYDROGENATION AND CYCLOHEXANOL DEHYDROGENATION

(75) Inventors: Kamaraju Seetha Rama Rao, Andhra Pradesh (IN); David Raju Burri, Andhra Pradesh (IN); Narayanan Sankarasubbier, Andhra Pradesh (IN); Mallanna Nagaraja Bhari, Andhra Pradesh (IN); Hari Padmasri Aytam, Andhra Pradesh (IN); Sivakumar Vasireddy, Andhra Pradesh (IN); Shashikala Veldurthi, Andhra Pradesh (IN); Seetharamulu Podila, Andhra Pradesh (IN); Sanapureddy Sreevardhan Reddy, Andhra Pradesh (IN)

(73) Assignee: Council of Scientific and Industrial Research, (IN)

( * ) Notice: Subject to any disclaimer, the term of this patent is extended or adjusted under 35 U.S.C. 154(b) by 0 days.

(21) Appl. No.: 11/022,398

(22) Filed: Dec. 23, 2004

(51) Int. Cl.
*C07C 45/29* (2006.01)
*C07D 307/02* (2006.01)

(52) U.S. Cl. .................. 568/361; 549/497; 549/503
(58) Field of Classification Search .............. None
See application file for complete search history.

(56) References Cited

U.S. PATENT DOCUMENTS

| 4,251,396 A | * | 2/1981 | Frainier et al. ............ 252/467 |
| 4,261,905 A | * | 4/1981 | Preobrazhenskaya et al. ............ 260/347.8 |
| 4,665,042 A | * | 5/1987 | Budge et al. ............ 502/61 |
| 5,198,592 A | * | 3/1993 | van Beijnum et al. ...... 568/885 |
| 5,591,873 A | * | 1/1997 | Bankmann et al. ......... 549/503 |
| 6,376,422 B1 | * | 4/2002 | McNabb et al. ............ 502/307 |

* cited by examiner

*Primary Examiner*—Sikarl A. Witherspoon
(74) *Attorney, Agent, or Firm*—Ostrolenk, Faber, Gerb & Soffen, LLP

(57) ABSTRACT

The present invention provides a catalytic process for the synthesis of furfuryl alcohol and cyclohexanone simultaneously over a copper based catalyst in vapour phase conditions by hydrogenation of furfural and dehydrogenation of cyclohexanol respectively.

10 Claims, No Drawings

VAPOR PHASE CATALYTIC PROCESS FOR SIMULTANEOUS FURFURAL HYDROGENATION AND CYCLOHEXANOL DEHYDROGENATION

FIELD OF THE INVENTION

The present invention relates to a catalytic process for simultaneous furfural hydrogenation and cyclohexanol dehydrogenation in vapor phase.

BACKGROUND OF THE INVENTION

Furfuryl alcohol is an important chemical, mainly used for the production of resins for bonding foundry sand to produce cores and molds for metal casting, corrosion-resistant mortar for installing acid proof brick, laminating resins for corrosion resistant fiberglass-reinforced equipment, resins for corrosion resistant furan polymer concrete, impregnating solutions and carbon binders. It is also used as nonreactive diluent for epoxy resins, modifier for phenolic and urea resins, oil-well sand consolidation, solvent, production of tetrahydro furfuryl alcohol and other chemical synthesis. It is also an important chemical intermediate for the manufacture of lysine, vitamin C, lubricant, dispersing agent and plastisizer.

Cyclohexanone is an industrially important chemical for the manufacture of caprolactum and adipic acid which are used in producing polyamide fiber in nylon-textiles.

Industrially, furfuryl alcohol is produced by hydrogenation of furfural either in liquid phase or in vapor phase. On the other hand, cyclohexanone is produced majorily in vapor phase by dehydrogenation of cyclohexanol. Both the processes employ copper based catalysts.

A number of methods are reported in patent literature on the preparation of catalysts useful for the separate hydrogenation of furfural and dehydrogenation of cyclohexanol.

Liquid phase hydrogenation of furfural under a pressure of 30 atm. over copper chromite catalysts were disclosed in U.S. Pat. Nos. 4,251,396, 4,302,397. Chinese patent CN1404922 discloses a catalyst comprising of CuO—$Cr_2O_3$—NiO for the liquid phase hydrogenation of furfural at 35 to 50 atm. and in the temperature range of 453–473 K. The vapor phase hydrogenation of furfural was disclosed in U.S. Pat. Nos. 4,261,905 and 5,591,873 wherein copper chromite promoted with alkali earth metals and copper deposited on pyrogenic $SiO_2$ respectively were employed as catalysts. In both the cases the reaction was carried out under pressure.

Vapour phase dehydrogenation of cyclohexanol to produce cyclohexanone over Cu—Cr based catalysts are disclosed in KR8300880 and U.S. Pat. No. 4,310,703. Processes for making Cu/ZnO or Cu/$SiO_2$ with promoters, suitable for dehydrogenation of cyclohexanol were disclosed in JP2000288395, RU210183, U.S. 2004087815, WO09810864. Process for making a multicomponent Cu based cyclohexanol dehydrogenation catalyst was disclosed in CN1056067. A process for making Cu on MgO with promoters for dehydrogenation reaction was disclosed in CN1235870. Liquid phase dehydrogenation of cyclohexanol under pressure was disclosed in Chinese patent CN1381434 and the corresponding method for catalyst making was disclosed in another Chinese patent CN1381435. A process for making a non Cu based catalyst comprising of ZnO—CaO or $CaCO_3$—$Cr_2O_3$ is disclosed in U.S. Pat. No. 6,376,422.

A process for making Cu based catalyst suitable for both hydrogenation and a dehydrogenation process separately was disclosed in GB patent 1097819.

The main drawbacks of the furfural hydrogenation processes mentioned above are that they require either to be operated under pressure or to use large amount of hydrogen along with furfural. Even though both furfural hydrogenation and cyclohexanol dehydrogenation processes employ mostly Cu based catalysts, there are no reports on the combined or simultaneous study of these two processes over a single catalyst system.

OBJECTS OF THE INVENTION

The main object of the invention is to provide a catalytic process for simultaneous furfural hydrogenation and cyclohexanol dehydrogenation in vapor phase conditions.

Another object of the invention is to provide a process wherein the use of external source of hydrogen is avoided for furfural hydrogenation due to self-generation of hydrogen, thereby saving on costs.

Another object of the invention is to provide a process wherein simultaneous furfural hydrogenation and cyclohexanol dehydrogenation takes place at atmospheric pressure.

Still another object of the invention is to provide a process wherein the equilibrium barrier for the dehydrogenation of cyclohexanol can be overcome.

Yet another object of the invention is to provide a process wherein the vapor phase hydrogenation of furfural and dehydrogenation of cyclohexanol are conducted on a copper-magnesia promoted by chromia catalyst prepared by simple techniques like coprecipitation and/or impregnation.

Another object of the invention is to provide a process with stable catalytic activity in simultaneous furfural hydrogenation and cyclohexanol dehydrogenation.

SUMMARY OF THE INVENTION

The present invention provides a catalytic process for the synthesis of furfuryl alcohol and cyclohexanone simultaneously over a copper based catalyst in vapour phase conditions by hydrogenation of furfural and dehydrogenation of cyclohexanol respectively.

Accordingly the present invention provides a catalytic process for the simultaneous synthesis of furfuryl alcohol and cyclohexanone by the hydrogenation of furfural and dehydrogenation of cyclohexanol respectively, the process comprising contacting a mixture of furfural and cyclohexanol with a copper based catalyst of the formula xCu—yMgO—$zCr_2O_3$, wherein x, y and z are the amounts in terms of weight percent of Cu, MgO and $Cr_2O_3$ respectively, under reaction conditions, collecting product streams obtained and separating furfuryl alcohol and cyclohexanone.

In one embodiment of the invention, the copper based catalyst has a Cu content in the range of 5 to 50 wt % preferably in the range of 10 to 25 wt %. $Cr_2O_3$ content in the range of 0 to 15 wt %, preferably in the range of 1 to 10 wt %, the balance being MgO.

In another embodiment of the invention, co-precipitation method is employed for preparing Cu—MgO and/or Cu—MgO—$Cr_2O_3$.

In another embodiment of the invention, the $Cr_2O_3$ is deposited on CuO—MgO by impregnation.

In yet another embodiment of the invention, the mixture of furfural and cyclohexanol is contacted with the copper based catalyst in vapor phase resulting in the hydrogenation of furfural by hydrogen released due to the dehydrogenation of cyclohexanol.

In another embodiment of the invention, the contacting is carried out in a quartz fixed bed vertical reactor (200 mm long and 8 mm i.d) placed in an electrically heatable cylindrical furnace, with about 1 g of the catalyst packed at the center of the reactor between two plugs of quartz wool being reduced in 6% $H_2$ and balance He flow at 523 K for 4 h followed by lowering the temperature of the reactor to 473 K and replacing the $H_2$/He by pure $N_2$ gas, the mixture of furfural and cyclohexanol being continuously pumped at a total liquid flow of 1 ml/h into the reactor, the resulting product stream being separated into cyclohexanone and furfuryl alcohol.

In another embodiment of the invention, the contacting is carried out in the absence of external hydrogen.

In yet another embodiment of the invention, the contacting is carried out at a temperature of about 473 K and at atmospheric pressure.

DETAILED DESCRIPTION OF THE INVENTION

In the process of the present invention involving hydrogenation of furfural and dehydrogenation of cyclohexanol processes over copper based catalysts, it is possible to conduct the two processes simultaneously.

The present invention resides in that no external source of hydrogen is required for the furfural hydrogenation, equilibrium barrier for the dehydrogenation of cyclohexanol can be overcome and since both the reactions are conducted in vapor phase, separation of catalyst from product mixture is easy and the method of making the catalyst employs simple techniques like co-precipitation and impregnation.

In the process of the present invention the operation of both furfural hydrogenation and cyclohexanol dehydrogenation at atmospheric pressure is disclosed. The equilibrium barrier for the dehydrogenation of cyclohexanol is overcome. The copper based catalyst is prepared by relatively simple techniques of co-precipitation and/or impregnation for making of copper based catalyst. The catalytic activity is stable.

Scientific Explanation

Even though hydrogenation of furfural to yield furfuryl alcohol appears to be simple, the nature of catalyst and the reaction conditions play an important role particularly in getting furfuryl alcohol selectively. Copper based catalysts are suitable for this reaction. The reaction temperature is critical and if it crosses a particular temperature (~473 K), ring hydrogenation may also lead to by-products.

$$C_4H_4OCHO + H_2 \rightarrow C_4H_4OCH_2OH \quad (1)$$

Thus for getting one mole of furfuryl alcohol, one mole of furfural and one mole of hydrogen molecule are required. Also two moles of reactants yield one mole of product and therefore this reaction is favorable under pressure.

On the other hand, dehydrogenation of cyclohexanol to cyclohexanone is limited by equilibrium constraints.

$$C_6H_{11}OH \leftrightarrows C_6H_{10}O + H_2 \quad (2)$$

It was reported that the equilibrium conversion of direct dehydrogenation of cyclohexanol (Ref: H. A. Cubberley and M. B. Muller, J. Am. Chem. Soc., 63 (1947) 1535) at 473 K was 45.22%.

The advantage of combining these two reactions are, that there is every possibility to overcome the equilibrium limitations in the second reaction and the hydrogen produced in the second reaction is sufficient to carryout the first reaction thereby there is no necessity to pump extra hydrogen externally for the first reaction.

The catalyst employed in this investigation is Cu—MgO—$Cr_2O_3$ wherein the Cu content is in the range of 5 to 50 wt. % preferably in the range of 10 to 25 weight percent. $Cr_2O_3$ content is 0 to 15 weight percent preferably in the range of 1 to 10 weight percent and the remaining is MgO. Coprecipitation method is employed for preparing Cu—MgO and/or Cu—MgO—$Cr_2O_3$ because by this method it is possible to get more CuO—MgO—$Cr_2O_3$ interacted species. $Cr_2O_3$ can also be deposited on CuO—MgO by impregnation technique.

Vapor phase hydrogenation of furfural was carried out in a quartz fixed bed vertical reactor (200 mm long and 8 mm i.d) placed in an electrically heatable cylindrical furnace. About 1 g of the catalyst packed at the center of the reactor between two plugs of quartz wool has been reduced in 6% $H_2$ (and balance He) flow at 523 K for 4 h followed by lowering the temperature of the reactor to 473 K and replacing the $H_2$/He by pure $N_2$ gas. Mixture of furfural and cyclohexanol (total liquid flow of 1 ml/h) with the help of a syringe pump is continuously pumped. The product mixture is collected in a receiver kept in an ice bath and it is analyzed at regular intervals by gas chromatograph with flame ionization detector.

The present invention is described with reference to the following examples that are explained by way of illustrations only and should not therefore be construed to limit the scope of the present work.

EXAMPLE—1

Approximately 230 ml of aqueous solution containing 8.36 g and 49.358 g of $Cu(NO_3)_2.3H_2O$ and $Mg(NO_3)_2.6H_2O$ respectively have been simultaneously precipitated using an aqueous solution containing 1M $K_2CO_3$ at a pH of 9. The coprecipitated mass was thoroughly washed with distilled water for three times and filtered. The resultant mass was impregnated with 2 ml of aqueous solution containing 0.53 g of $Cr(NO_3)_3.9H_2O$. The excess water was evaporated over a hot water bath and the sample was then dried overnight in an oven at 383 K followed by calcination in air at 723 K for 4 h.

This catalyst has been tested for furfural hydrogenation and cyclohexanol dehydrogenation simultaneously. In the activity experiment, the molar ratio of furfural and cyclohexanol is maintained at 1:5. Following are the results obtained.

| S. No. | Reaction Time, h | Furfural conversion, % | Selectivity of furfuryl alcohol, % (w.r.t. furfural conversion) | Cyclohexanol conversion, % | Selectivity of cyclohexanone, % (w.r.t. cyclohexanol conversion) |
|---|---|---|---|---|---|
| 1 | 1 | 100  | 100 | 58.2 | 100 |
| 2 | 2 | 89.5 | 100 | 49.0 | 100 |
| 3 | 3 | 83.4 | 100 | 42.6 | 100 |

EXAMPLE—2

The catalyst mentioned in example—1 has been tested for the furfural hydrogenation and cyclohexanol dehydrogenation simultaneously. In the activity experiment, the molar ratio of furfural and cyclohexanol is maintained at 1:3.5. Following are the results obtained.

| S. No. | Reaction Time, h | Furfural conversion, % | Selectivity of furfuryl alcohol, % (w.r.t. furfural conversion) | Cyclohexanol conversion, % | Selectivity of cyclohexanone, % (w.r.t. cyclohexanol conversion) |
|---|---|---|---|---|---|
| 1 | 1 | 70.8 | 100 | 58.4 | 100 |
| 2 | 2 | 76.3 | 100 | 49.2 | 100 |
| 3 | 3 | 78.3 | 100 | 49.1 | 100 |

EXAMPLE—3

The catalyst mentioned in example—1 has been tested for the furfural hydrogenation and cyclohexanol dehydrogenation simultaneously.

In the activity experiment, the molar ratio of furfural and cyclohexanol is maintained at 1:1.7. Following are the results obtained.

| S. No. | Reaction Time, h | Furfural conversion, % | Selectivity of furfuryl alcohol, % (w.r.t. furfural conversion) | Cyclohexanol conversion, % | Selectivity of cyclohexanone, % (w.r.t. cyclohexanol conversion) |
|---|---|---|---|---|---|
| 1 | 1 | 76.8 | 100 | 50.6 | 100 |
| 2 | 2 | 63.8 | 100 | 37.7 | 100 |
| 3 | 3 | 57.8 | 100 | 25.6 | 100 |

EXAMPLE—4

Approximately 222 ml of ethanol solution containing 8.36 g, 47.45 g and 2.11 g of Cu $(NO_3)_2 \cdot 3H_2O$, Mg $(NO_3)_2 \cdot 6H_2O$ and $Cr(NO_3)_3 \cdot 9H_2O$ respectively have been simultaneously precipitated using 20 weight % tetraethylammonium hydroxide solution at a pH of 9. The coprecipitated mass has been thoroughly washed with ethanol for three times and filtered. The sample was then dried in an oven at 383 K for overnight followed by calcination in air at 723 K for 4 h.

This catalyst has been tested for the furfural hydrogenation and cyclohexanol dehydrogenation simultaneously. In the activity experiment, the molar ratio of furfural and cyclohexanol is maintained at 1:5. Following are the results obtained.

| S. No. | Reaction Time, h | Furfural conversion, % | Selectivity of furfuryl alcohol, % (w.r.t. furfural conversion) | Cyclohexanol conversion, % | Selectivity of cyclohexanone, % (w.r.t. cyclohexanol conversion) |
|---|---|---|---|---|---|
| 1 | 1 | 60.1 | 100 | 36.5 | 100 |
| 2 | 2 | 80.4 | 100 | 40.5 | 100 |
| 3 | 3 | 83.3 | 100 | 41.0 | 100 |
| 4 | 4 | 88.4 | 100 | 39.5 | 100 |
| 5 | 5 | 87.7 | 100 | 37.1 | 100 |
| 6 | 6 | 88.8 | 100 | 34.7 | 100 |
| 7 | 7 | 88.2 | 100 | 36.5 | 100 |

EXAMPLE—5

The catalyst mentioned in example—1 has been tested for the furfural hydrogenation. In the activity experiment, furfural (liquid) and $H_2$ (gas) feed rates are maintained at 1.2 ml/h and 1 l/h respectively and the reaction temperature is maintained at 453 K. Following are the results obtained.

| S. No. | Reaction Time, h | Furfural conversion, % | Selectivity of furfuryl alcohol, % (w.r.t. furfural conversion) |
|---|---|---|---|
| 1 | 1 | 82.0 | 100 |
| 2 | 2 | 80.9 | 100 |
| 3 | 3 | 78.4 | 100 |
| 4 | 4 | 77.4 | 100 |
| 5 | 5 | 77.1 | 100 |
| 6 | 6 | 77.0 | 100 |

EXAMPLE—6

The catalyst mentioned in example—1 has been tested for the furfural hydrogenation. In the activity experiment, furfural (liquid) and $H_2$ (gas) feed rates are maintained at 2 ml/h and 1 l/h respectively and the reaction temperature is maintained at 473 K. Following are the results obtained.

| S. No. | Reaction Time, h | Furfural conversion, % | Selectivity of furfuryl alcohol, % (w.r.t. furfural conversion) |
|---|---|---|---|
| 1 | 1 | 60.2 | 100 |
| 2 | 2 | 61.0 | 100 |
| 3 | 3 | 57.9 | 100 |
| 4 | 4 | 63.5 | 100 |
| 5 | 5 | 58.3 | 100 |
| 6 | 6 | 59.6 | 100 |

EXAMPLE—7

The catalyst mentioned in example—1 has been tested for the cyclohexanol dehydrogenation.

In the activity experiment, cyclohexanol (liquid) and $N_2$ (gas) feed rates are maintained at 1 ml/h and 0.52 l/h respectively and the reaction temperature is maintained at 453 K. Following are the results obtained.

| S. No. | Reaction Time, h | Cyclohexanol conversion, % | Selectivity of cyclohexanone, % (w.r.t. cyclohexanol conversion) |
|---|---|---|---|
| 1 | 1 | 34.2 | 100 |
| 2 | 2 | 31.8 | 100 |
| 3 | 3 | 30.8 | 100 |
| 4 | 4 | 30.4 | 100 |
| 5 | 5 | 30.9 | 100 |
| 6 | 6 | 31.7 | 100 |

EXAMPLE—8

The catalyst mentioned in example—1 has been tested for the cyclohexanol dehydrogenation.

In the activity experiment, cyclohexanol (liquid) and $N_2$ (gas) feed rates are maintained at 1 ml/h and 0.52 l/h respectively and the reaction temperature is maintained at 473 K. Following are the results obtained.

| S. No. | Reaction Time, h | Cyclohexanol conversion, % | Selectivity of cyclohexanone, % (w.r.t. cyclohexanol conversion) |
|---|---|---|---|
| 1 | 1 | 44.2 | 100 |
| 2 | 2 | 37.9 | 100 |
| 3 | 3 | 40.9 | 100 |
| 4 | 4 | 40.9 | 100 |
| 5 | 5 | 41.2 | 100 |
| 6 | 6 | 38.7 | 100 |

EXAMPLE—9

The catalyst mentioned in example—1 has been tested for the cyclohexanol dehydrogenation.

In the activity experiment, cyclohexanol (liquid) and $N_2$ (gas) feed rates are maintained at 1 ml/h and 0.52 l/h respectively and the reaction temperature is maintained at 498 K. Following are the results obtained.

| S. No. | Reaction Time, h | Cyclohexanol conversion, % | Selectivity of cyclohexanone, % (w.r.t. cyclohexanol conversion) |
|---|---|---|---|
| 1 | 1 | 52.2 | 100 |
| 2 | 2 | 53.8 | 100 |
| 3 | 3 | 56.8 | 100 |
| 4 | 4 | 55.8 | 100 |
| 5 | 5 | 53.2 | 100 |
| 6 | 6 | 54.9 | 100 |

EXAMPLE—10

The catalyst mentioned in example—1 has been tested for the cyclohexanol dehydrogenation.

In the activity experiment, cyclohexanol (liquid) and $N_2$ (gas) feed rates are maintained at 1 ml/h and 0.52 l/h respectively and the reaction temperature is maintained at 523 K. Following are the results obtained.

| S. No. | Reaction Time, h | Cyclohexanol conversion, % | Selectivity of cyclohexanone, % (w.r.t. cyclohexanol conversion) |
|---|---|---|---|
| 1 | 1 | 61.1 | 100 |
| 2 | 2 | 67.0 | 100 |
| 3 | 3 | 64.2 | 100 |
| 4 | 4 | 67.7 | 100 |
| 5 | 5 | 66.9 | 100 |
| 6 | 6 | 66.0 | 100 |

ADVANTAGES OF THE INVENTION

1. The process of the reaction comprises simultaneous hydrogenation of furfural and dehydrogenation of cyclohexanol over a single catalyst system.
2. The contacting is carried out under atmospheric pressure and under vapour phase conditions.
3. External source of hydrogen for hydrogenation is not required since hydrogen is generated during the contacting due to dehydrogenation of cyclohexanol leading to saving in costs.

We claim:

1. A catalytic process for the simultaneous synthesis of furfuryl alcohol and cyclohexanone by the hydrogenation of furfural and dehydrogenation of cyclohexanol respectively, the process comprising contacting a mixture of furfural and cyclohexanol with a Cu based catalyst of the formula xCu—yMgO—zCr$_2$O$_3$, wherein x, y and z are the amounts in terms of weight percent of Cu, MgO and Cr$_2$O$_3$ respectively, under reaction conditions, collecting product streams obtained and separating furfuryl alcohol and cyclohexanone.

2. A process as claimed in claim 1 wherein the Cu based catalyst has a Cu content in the range of 5 to 50 wt %, Cr$_2$O$_3$ content in the range of 0 to 15 wt %, balance being MgO.

3. A process as claimed in claim 2 wherein the copper based catalyst has a Cu content in the range of 10 to 25 wt %, Cr$_2$O$_3$ content in the range of 1 to 10 wt %, the balance being MgO.

4. A process as claimed in claim 1 wherein the catalyst is selected from the group consisting of Cu—MgO and Cu—MgO—Cr$_2$O$_3$ and is prepared by co-precipitation.

5. A process as claimed in claim 1 wherein the Cr$_2$O$_3$ is deposited on CuO—MgO by impregnation.

6. A process as claimed in claim 1 wherein the mixture of furfural and cyclohexanol is contacted with the copper based catalyst in vapor phase resulting in the hydrogenation of furfural by hydrogen released due to the dehydrogenation of cyclohexanol.

7. A process as claimed in claim 1 wherein the contacting is carried out in a quartz fixed bed vertical reactor placed in an electrically heatable cylindrical furnace, with about 1 g of the catalyst packed at the center of the reactor between two plugs of quartz wool being reduced in 6% H$_2$ and balance He flow at 523 K for 4 h followed by lowering the temperature of the reactor to 473 K and replacing the H$_2$/He by pure N$_2$ gas, the mixture of furfural and cyclohexanol being continuously pumped at a total liquid flow of 1 ml/h into the reactor, resulting product stream being separated into cyclohexanone and furfuryl alcohol.

8. A process as claimed in claim 1 wherein the contacting is carried out in the absence of external hydrogen.

9. A process as claimed in claim 1 wherein the contacting is carried out at a temperature of about 473 K.

10. A process as claimed in claim 1 wherein the contacting is carried out at atmospheric pressure.

* * * * *